(12) United States Patent
Park et al.

(10) Patent No.: US 6,706,895 B1
(45) Date of Patent: Mar. 16, 2004

(54) 4-METHOXYBIPHENYL HYDRAZONE DERIVATIVES

(75) Inventors: Sheldon B. Park, Waterloo (CA); Gaik-Lean Chee, Guelph (CA); Mark A. Dekeyser, Waterloo (CA)

(73) Assignees: Uniroyal Chemical Company, Inc., Middlebury, CT (US); Crompton Co./Cie, Elmira (CA)

( * ) Notice: Subject to any disclaimer, the term of this patent is extended or adjusted under 35 U.S.C. 154(b) by 0 days.

(21) Appl. No.: 10/294,315

(22) Filed: Nov. 14, 2002

(51) Int. Cl.⁷ .................. C07D 333/12; C07C 241/00
(52) U.S. Cl. .................. 549/75; 564/314; 564/251; 564/250
(58) Field of Search .................. 549/75; 564/314, 564/251, 250

(56) References Cited

U.S. PATENT DOCUMENTS

| | | | | |
|---|---|---|---|---|
| 3,642,813 A | * | 2/1972 | Geigy | 548/255 |
| 4,732,904 A | * | 3/1988 | Morgan | 514/357 |
| 4,864,032 A | | 9/1989 | Demers | 548/359 |
| 5,367,093 A | | 11/1994 | Dekeyser et al. | 560/27 |
| 5,461,076 A | * | 10/1995 | Stanek et al. | 514/632 |
| 5,650,444 A | * | 7/1997 | Caggiano et al. | 514/640 |
| 6,093,843 A | | 7/2000 | Chee et al. | 560/27 |
| 6,235,936 B1 | | 5/2001 | Buchwald et al. | 564/386 |
| 6,278,022 B1 | * | 8/2001 | Jin | 564/411 |
| 6,489,512 B1 | * | 12/2002 | Hicks et al. | 564/310 |
| 6,610,715 B1 | * | 8/2003 | Youn et al. | 514/354 |
| 6,613,942 B1 | * | 9/2003 | Ling et al. | 564/161 |

FOREIGN PATENT DOCUMENTS

WO 99/43643 9/1999

OTHER PUBLICATIONS

Wagaw et al., J. Am. Chem. Soc. 120(26):6621–6622 (1998).
Mitchell, J. Org. Chem. 59:682–687 (1994).
Lenarsic, J. Org. Chem. 64:2258–2563 (1999).

* cited by examiner

Primary Examiner—Deborah C. Lambkin
(74) Attorney, Agent, or Firm—Daniel Reitenbach

(57) ABSTRACT

Disclosed herein is a compound having the formula:

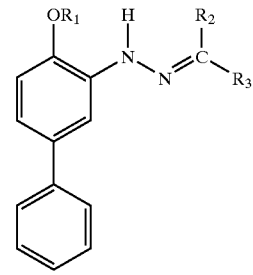

wherein $R_1$ is alkyl and $R_2$ and $R_3$ are independently selected aryl groups. Also disclosed is a method of making bifenazate using the compound as an intermediate.

23 Claims, No Drawings

4-METHOXYBIPHENYL HYDRAZONE DERIVATIVES

BACKGROUND OF THE INVENTION

1. Field of the Invention

This invention relates to certain 4-methoxybiphenyl hydrazide derivatives useful as intermediates in the preparation of isopropyl-2-(4methoxy-[1,1'-biphenyl]-3-yl) hydrazine carboxylate (Bifenazate).

2. Description of Related Art

Destruction by insects, acarids and nematodes presents a serious problem to agriculture. A wide variety of field crops are in need of protection from nematodes, acarids, and insects, including such valuable crops as soybeans, corn, peanuts, cotton, alfalfa, rice, and tobacco. In addition, vegetables, such as tomatoes, potatoes, sugar beets, carrots, peas, and the like, as well as fruits, nuts, ornamentals, and seed bed crops, such as apples, peaches, almonds, citrus fruit, and grapes may also require protection from the ravages of such pests.

Consequently, the development of new, more effective methods for preparing known pesticides, including insecticides, acaricides, and nematicides represents an ongoing scientific activity. More particularly, the development of improved methods for the preparation of known pesticides that are effective as both ovicides and larvicides are of interest.

One such pesticide is Bifenazate, which can be prepared by a six step procedure from 4-hydroxybiphenyl hydrazine, which is, in turn, prepared from a diazonium salt. This method is laborious, costly, and requires careful attention to the sensitive key steps, i.e., the preparation and reduction of the diazonium salt.

U.S. Pat. No. 5,367,093 describes a method for the preparation of the miticidal phenylhydrazine derivative, isopropyl-2-(4methoxy-[ 1,1'-biphenyl]-3-yl)hydrazine carboxylate (bifenazate), using a six-step procedure comprising the undesirable steps of preparation and reduction of a diazoniun salt.

U.S. Pat. No. 6,093,843 discloses compounds having the formula:

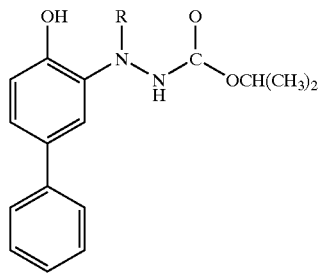

wherein R is hydrogen or $CO_2CH(CH_3)_2$, useful as intermediates in the preparation of the miticide bifenazate, methods for their preparation, and methods for the preparation of the bifenazate.

U.S. Pat. No. 6,235,936 discloses a method for the transition metal-catalyzed arylation, or vinylation, of hydrazines, hydrazones, and the like. Additionally, a strategy is provided, the cornerstone of which is a transition metalatalyzed arylation or vinylation method, for the synthesis of indoles, carbazoles, and the like. It is said that the methods and strategies of the invention may be utilized in standard, parallel, and combinatorial synthetic protocols. (See also the related WO 99/43643 and Wagaw et al., *J. Am. Chem. Soc.* 120(26):6621-2 (1998).)

Additionally, certain phenylhydrazine derivatives can be prepared using the methods described in U.S. Pat. No. 4,864,032 (amination of Grignard); in Mitchell, *J. Org. Chem.* 59: 682 (1994) (amination of electron-rich arenes); and in Lenarsic, *J. Org. Chem.* 64: 2558 (1999) (by electrophilic azodicarboxylates).

The disclosures of the foregoing are incorporated herein by reference in their entirety.

SUMMARY OF THE INVENTION

It is an object of the present invention to provide new intermediates useful in the preparation of bifenazate.

It is another object of the present invention to provide a new method for the preparation of bifenazate.

It is another object of the present invention to prepare aryl hydrazones of 4-alkoxybiphenyl that are useful as intermediates for the preparation of bifenazate, whereby the inefficient preparation and reduction of a diazonium salt intermediate can be avoided.

These and other objects are accomplished by means of the present invention, which relates to compounds (hereinafter referred to as Compound I) that are useful intermediates for the preparation of bifenazate having the formula:

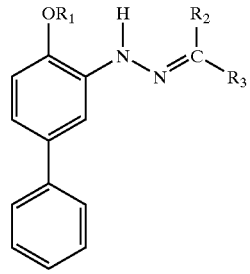

wherein $R_1$ is alkyl and $R_2$ and $R_3$ are independently selected aryl groups.

Thus, the present invention is directed to a compound having the formula:

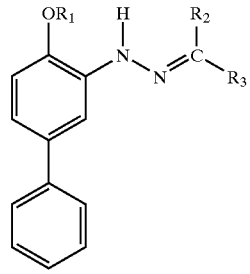

wherein $R_1$ is alkyl and $R_2$ and $R_3$ are independently selected aryl groups.

In another aspect, the present invention is directed to a method for preparing bifenazate comprising:

A) coupling a 3-halo-4-methoxybiphenyl, preferably 3-bromo-4-methoxybiphenyl, with a diarylhydrazone in the presence of a coupling catalyst, a ligand, a first base, and a solvent at or above room temperature to form a compound of the formula I:

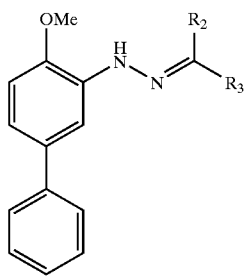

B) treating the compound of formula I with a mixture of hydrochloric acid and ethyl acetate to give a compound of formula II:

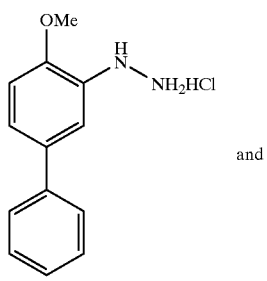

and

C) converting the compound of formula II to bifenazate by reaction with an alkali metal hydroxide, preferably sodium hydroxide, followed by reaction with an isopropyl haloformate, preferably isopropyl chloroformate, in the presence of a second base.

DESCRIPTION OF THE PREFERRED EMBODIMENTS

As disclosed above, the present invention relates to compounds having the formula:

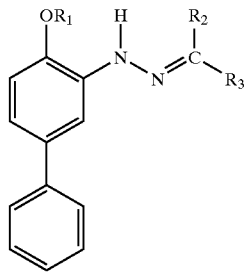

wherein $R_1$ is alkyl and $R_2$ and $R_3$ are independently selected aryl groups.

$R_1$ is preferably a lower alkyl, which may, if desired, be branched. It is more preferably a lower alkyl of from one to four carbon atoms, e.g., methyl, ethyl, n-propyl, isopropyl, n-butyl, isobutyl, sec-butyl, or tert-butyl. Thus, $OR_1$ in the above formula will be an alkoxy group, preferably methoxy, ethoxy, n-propoxy, isopropoxy, n-butoxy, isobutoxy, sec-butoxy, or tert-butoxy. It is especially preferred that $R_1$ be methyl and $OR_1$ be methoxy.

$R_2$ and $R_3$ of Compound I are independently selected aryl groups, which may be substituted or unsubstituted. The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyriridine, and the like. Those aryl groups having heteroatoms in the ring structure may also be referred to as "aryl heterocycles" or "heteroaromatics". The aromatic ring can be substituted at one or more ring positions with such substituents as, for example, halogen, alkyl, aralkyl, alkenyl, alkynyl, cycloalkyl, nitro, alkylthio, heterocyclyl, aromatic or heteroaromatic moieties, $-CF_3$, $-CN$, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can, if desired, be cycloalkyls, cycloalkenyls, cycloalkynyls, aryls, and/or heterocyclyls.

It is preferred that both $R_2$ and $R_3$ be phenyl, either or both of which can optionally be substituted, preferably with one or more groups selected from the group consisting of halo, alkoxy, haloalkyl, thienyl, fluorenyl, and halofluorenyl.

The compounds employed in the practice of the present invention can be prepared as described below and as shown in Scheme 1.

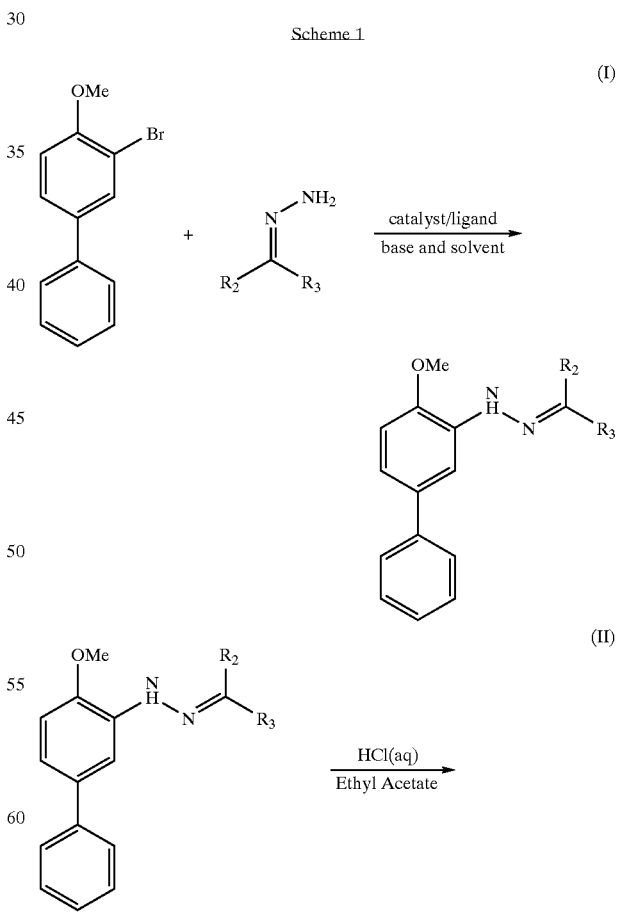

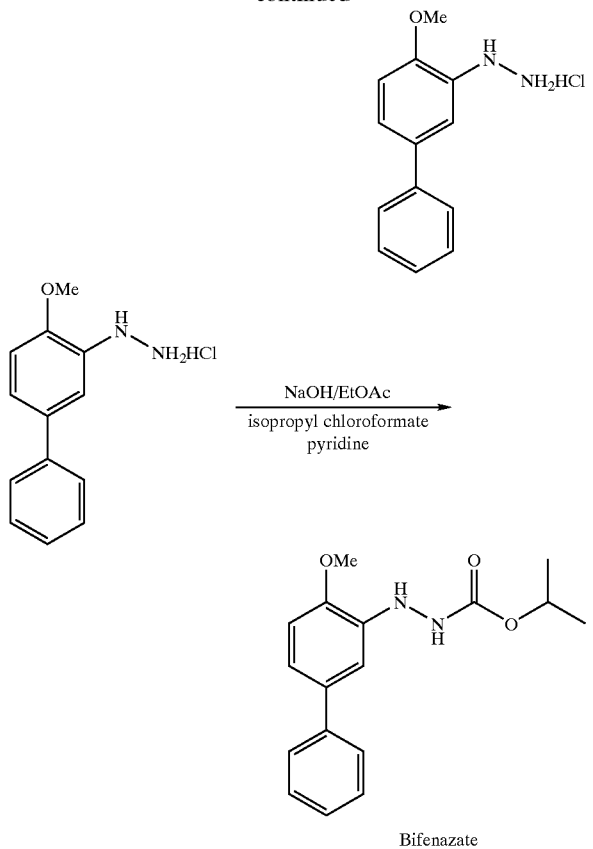

Bifenazate

3-Bromo4-methoxybiphenyl is coupled with a diarylhydrazone using a suitable coupling catalyst in the presence of a suitable ligand and a base in a suitable solvent at room or elevated temperature to form Compound I.

The coupling catalyst is preferably a transition metal catalyst including soluble or insoluble complexes of platinum, palladium, and nickel. Nickel and palladium are particularly preferred and palladium is most preferred. Suitable catalysts include, but are not limited to, palladium acetate, tris(dibenzylideneacetone)dipalladium, nickel diphenylphosphinoferrocene, and the like.

The ligand is preferably a phosphine ligand that is commercially available or can be prepared by methods similar to processes known in the art. The phosphines can, for example, be tri-tert-butylphosphine, 2-(di-tert-butylphophino)biphenyl, 2,2-'(dicyclohexylphosphino) biphenyl, or a bidentate phosphine ligand, such as 2,2'-bis(diphenylphosphino)-1,1'-binaphthyl, 1,2-bis(dimethylphosphino)ethane, 1,2-bis(diethylphosphinoethane, 1,2-bis(dipropylphosphino) ethane, 1,2-bis(diisopropylphosphino)ethane, 1,2-bis(dibutyl-phosphinocthane, 1,2-bis(dicyclohexylphosphino) ethane, 1,3-bis(dicyclohexylphosphino)propane, 1,3-bis(diiso-propylphosphino)propane, 1,4-bis(diisopropylphosphino)-butane, or 2,4-bis(dicyclohexylphosphino)pentane.

Bis(phosphine) ligands are particularly preferred. Suitable bis(phosphine) compounds include, but are not limited to, (±)-2,2'-bis(diphenylphosphino)-1,1'-binaphthyl (and separate enantiomers), (±)-2,2'-bis(di-p-tolylphosphino)-1,1,'-binaphthyl (and separate enantiomers), 1,1'-bis(diphenylphosphino)ferrocene, 1,3-bis(diphenylphosphino) propane, 1,2-bis(diphenylphosphino)benzene, 2,2'-bis(diphenylphosphino)diphenyl ether, and 1,2-bis(diphenylphosphino)ethane.

The most preferred ligands for use in the practice of the present invention include 2,2'-bis(diphenylphosphino)-1,1'-binaphthyl, bis {2-(diphenylphosphino)phenyl}ether, 1-(N, N-dimethylamino)-1'-(dicyclohexylphosphino)biphenyl, 1,1'-bis(diphenylphosphino)ferrocene, and the like.

The base employed in the coupling reaction can, for example, be an alkoxide, such as alkali metal alkoxides, e.g., sodium tert-butoxide; an alkali metal or alkaline earth carbonate or phosphate (e.g. sodium, magnesium, calcium, barium, potassium carbonate or phosphate). Preferred bases for use in the practice of the present invention include sodium t-butoxide, cesium carbonate, and potassium phosphate.

Suitable solvents include ethers, such as diethyl ether, 1,2-dimethoxyethane, diglyme, t-butyl methyl ether, tetrahydrofuiran, and the like; halogenated solvents, such as chloroform, dichloromethane, dichloroethane, chlorobenzene, and the like; aliphatic or aromatic hydrocarbon solvents, such as benzene, xylene, toluene, hexane, pentane, and the like; esters and ketones, such as ethyl acetate, acetone, and 2-butanone; polar aprotic solvents, such as acetonitrile, dimethylsulfoxide, dimethylformamide, and the like; or combinations of two or more solvents. Toluene, dimethoxyethane, and tetrahydrofuran are preferred.

In general, it will be desirable that the coupling reaction be run using mild conditions that will not adversely affect the reactants, the catalyst, or the product. The coupling reaction will usually be run at temperatures ranging from room temperature, e.g., about 20° C., to about 300° C., preferably from about 200° C. to about 150° C.

Compound I can then be treated with a mixture of hydrochloric acid and ethyl acetate to give hydrazine intermediate II, which can be converted to bifenazate by reaction with sodium hydroxide followed by reaction with isopropyl chloroformate in the presence of a base, e.g., pyridine. Compound II is an intermediate in a known method for preparing bifenazate, and the method for its conversion to bifenazate is described in U.S. Pat. No. 5,367,093.

The advantages and the important features of the present invention will be more apparent from the following examples.

EXAMPLE 1

Methanone, Diphenyl-, (4-Methoxy-[1,1'-biphenyl]-3-yl)hydrazone

3-Bromo-4-4-methoxybiphenyl (0.52 gram), palladium acetate (6.7 mg), 2,2'-bis(diphenylphosphino)-1,1'-binaphthyl (28 mg), sodium tert-butoxide (0.29 gram), and benzophenone hydrazone (0.43 gram) were weighed into a reaction vessel and placed under a nitrogen atmosphere. Toluene (5 mL) was added and the mixture was heated on a steam bath for 16 hours, then at 120° C. for 4 hours. The mixture was cooled, diluted with ethyl acetate (15 ml), washed with water, dried over sodium sulfate, and concentrated to give Compound I, methanone, diphenyl-, (methoxy-{1,1'-biphenyl}-3-yl)hydrazone, (0.61 gram) as a beige solid. $^1$H nmr (CDCl$_3$)δ8.0–6.8 (m, 19 H), 3.6 (s, s H). EIMS m/z 378.

Other species within the scope of Compound I were prepared. Their names and 1H NMR data are shown in Table 1.

TABLE 1

| Name | 1H NMR Data {chemical shift (multiplicity, integration)} |
|---|---|
| Methanone, diphenyl-, (4-methoxy-{1,1'-biphenyl}-3-yl)hydrazone | 8.0–6.8(m, 19H), 3.6(s, 3H) |
| Methanone, bis(4-methoxyphenyl)-, (4-methoxy-{1,1'-biphenyl}-3-yl)hydrazone | 8.0–6.8(m, 18H), 3.9(s, 3H), 3.8(s, 3H), 3.7(s, 3H) |
| Methanone, bis(3-(trifluoromethyl)phenyl}-, (4-methoxy-{1,1'-biphenyl}-3-yl)hydrazone | 8.2–6.8(m, 18H), 3.8(s, 3H) |
| 9H-fluoren-9-one, (4-methoxy-{1,1'-biphenyl}-3-yl)hydrazone | 9.4(s, 1H), 8.0–7.0(m, 16H), 4.0(s, 3H) |
| Methanone,(4-fluorophenyl)-2-thienyl-, (4-methoxy-{1,1'-biphenyl}-3-yl)hydrazone | 8.0–6.8(m, 16H), 3.9(s, 1H), 3.8(s, 2H) |
| 9H-fluoren-9-one, 2,7-dichloro-, (4-methoxy-{1,1'-biphenyl}-3-yl)hydrazone | 10.0(s, 1H), 8.0–7.0(m, 14H), 4.0(s, 3H) |

The structural formula of methanone, diphenyl-, (4methoxy-{1,1'-biphenyl}-3-yl)hydrazone is:

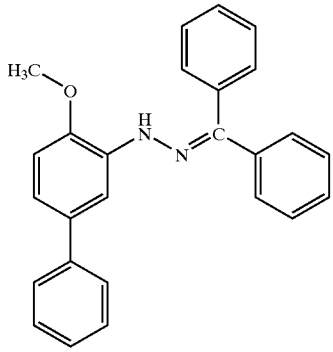

The structural formula of methanone, bis(4-methoxyphenyl)-, (4-methoxy-{1,1'-biphenyl}-3-yl)hydrazone is:

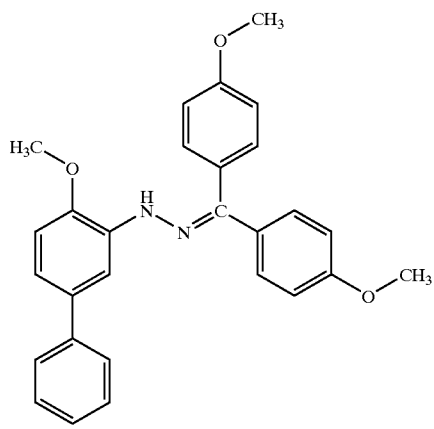

The structural formula of methanone, bis{3-(trifluoromethyl)phenyl}-, (4-methoxy-{1,1'-biphenyl}-3-yl)hydrazone is:

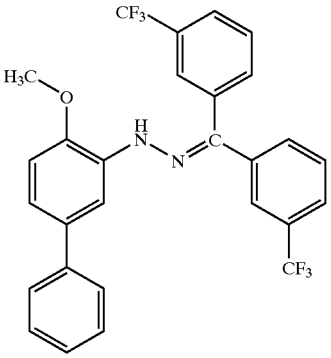

The structural formula of 9H-fluoren-9one, (4-methoxy-{1,1'-biphenyl}-3-yl)hydrazone is:

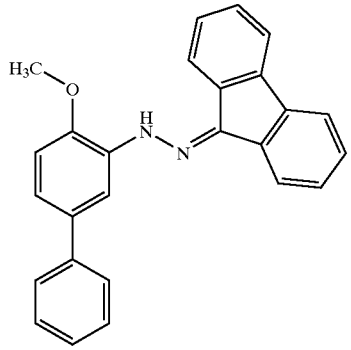

The structural formula of methanone, (4-fluorophenyl)-2-thienyl-,(4-methoxy-{1,1'biphenyl}-3-yl)hydrazone is:

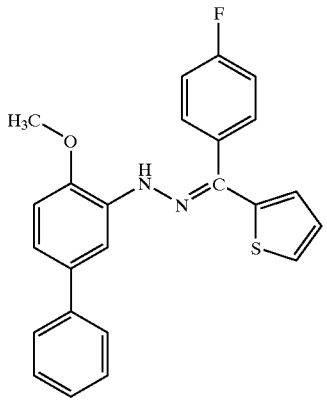

The structural formula of 9H-fluoren-9-one, 2,7-dichloro-,(4-methoxy-{1,1-biphenyl}-3-yl)hydrazone is:

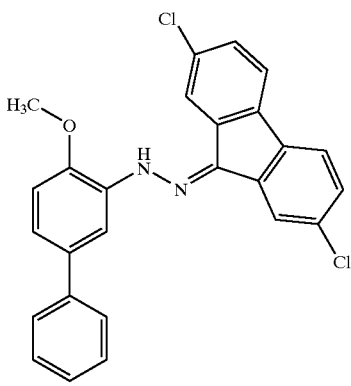

EXAMPLE 2

Bifenazate

To a suspension of Compound I (0.6 gram) in ethyl acetate (3 mL) was added 0.5 mL of concentrated hydrochloric acid. The mixture was stirred at room temperature for 16 hours and then heated to reflux for 1.5 hours. The mixture was cooled, filtered, and washed with ethyl acetate to give 0.29 gram of an off-white solid. This material was stirred in 2 M NaOH (aq) (5 mL) for 20 minutes and then ethyl acetate (10 mL) was added and stirring was continued for 10 minutes. More ethyl acetate was added (15 mL) and the phases separated. The ethyl acetate phase was washed with brine, dried over sodium sulfate and concentrated. The residue was dissolved in toluene (3 mL) and cooled in ice. Pyridine (0.19 mL) was added followed by a one molar solution of isopropyl chloroformate in toluene (1.3 mL). The mixture was stirred for 30 minutes and then extracted with water and concentrated. The residue was then co-distilled with toluene to give bifenazate (0.32 gram) which was confirmed by comparison to an authentic sample.

In view of the many changes and modifications that can be made without departing from principles underlying the invention, reference should be made to the appended claims for an understanding of the scope of the protection to be afforded the invention.

What is claimed is:

1. A compound having the formula:

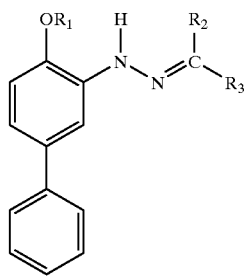

wherein $R_1$ is alkyl and $R_2$ and $R_3$ are independently selected aryl groups.

2. The compound of claim 1 wherein $R_1$ is a lower alkyl of from one to four carbon atoms.

3. The compound of claim 2 wherein $R_1$ is methyl.

4. The compound of claim 1 wherein at least one of $R_2$ anid $R_1$ is selected from the group consisting of 5-, 6- and 7-membered single-ring aromatic groups having from zero to four heteroatoms.

5. The compound of claim 4 wherein at least one of $R_2$ anid $R_3$ is selected from the group consisting of benzene, pyrrole, furan, thiophene, imidazole, oxazole, thiazole, triazole, pyrazole, pyridine, pyrazine, pyridazine, and pyrimidine.

6. The compound of claim 3 wherein at least one of $R_2$ and $R_3$ is selected from the group consisting of 5-, 6- and 7-membered single-ring aromatic groups having from zero to four heteroatoms.

7. The compound of claim 6 wherein at least one of $R_2$ and $R_3$ is selected from the group consisting of benzene, pyrrole, furan, thiophene, inidazole, oxazole, thiazole, triazole, pyrazole, pyridine, pyrazine, pyridazine, and pyrimidine.

8. The compound of claim 1 wherein at least one of $R_2$ and $R_3$, or $R_2$ and $R_3$ taken together, comprise a polycyclic ring system having two or more cyclic rings in which two or more carbons are common to two adjoining rings and wherein at least one of the rings is aromatic.

9. The compound of claim 3 wherein at least one of $R_2$ and $R_3$, or $R_2$ and $R_3$ taken together, comprise a polycyclic ring system having two or more cyclic rings in which two or more carbons are common to two adjoining rings and wherein at least one of the rings is aromatic.

10. The compound of claim 1 wherein said compound is selected from the group consisting of methanone, diphenyl-, (4-methoxy-{1,1'-biphenyl}-3-yl)hydrazone; methanone, bis(4methoxyphenyl)-, (4-methoxy-{1,1'-biphenyl}-3-yl) hydrazone; methanone, bis{3-(trifluoromethyl)phenyl}-, (4-methoxy-{1,1'-biphenyl}-3-yl)hydrazone; 9H-fluoren-9-one, (4-methoxy-{1,1'-biphenyl}-3-yl)hydrazone; methanone, (4-fluorophenyl)-2-thienyl-, (4-methoxy-{1,1'-biphenyl}-3-yl)hydrazone; and 9H-fluoren-9one, 2,7-dichloro-, (4-methoxy-{1,1'-biphenyl}-3-yl)hydrazone.

11. A method for preparing bifenazate comprising:

A) coupling a 3-halo-4-methoxybiphenyl with a diarylhydrazone in the presence of a coupling catalyst, a ligand, a first base, and a solvent at or above room temperature to form a compound of the formula I;

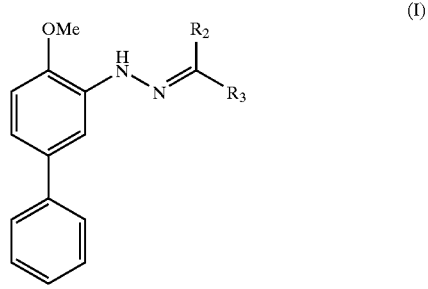

(B) treating the compound of formula I with a mixture of hydrochloric acid and ethyl acetate to give a compound of formula II:

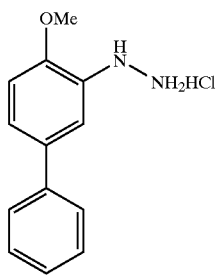

(II)

and

C) converting the compound of formula II to bifenazate by reaction with an alkali metal hydroxide followed by reaction with isopropyl haloformate in the presence of a second base.

12. The method of claim 11 wherein at least one of $R_2$ and $R_3$ is selected from the group consisting of 5-, 6- and 7-membered single-ring aromatic groups having from zero to four heteroatoms.

13. The method of claim 11 wherein at least one of $R_2$ and $R_3$ is selected from the group consisting of benzene, pyrrole, furan, thiophene, imidazole, oxazole, thiazole, triazole, pyrazole, pyridine, pyrazine, pyridazine, and pyrimidine.

14. The method of claim 11 wherein at least one of $R_2$ and $R_3$, or $R_2$ and $R_3$ taken together, comprise a polycyclic ring system having two or more cyclic rings in which two or more carbons are common to two adjoining rings and wherein at least one of the rings is aromatic.

15. The method of claim 11 wherein the compound of formula I is selected from the group consisting of methanone, diphenyl-, (4methoxy-{1,1'-biphenyl}-3-yl)hydrazone; methanone, bis(4-methoxyphenyl)-, (4-methoxy-{1,1'-biphenyl}-3-yl)hydrazone; methanone, bis{3-(trifluoromethyl)phenyl}-, (4-methoxy-{1,1'-biphenyl}-3-yl)hydrazone; 9H-fluoren-9-one, (4-methoxy-{1,1'-biphenyl}-3-yl)hydrazone; methanone, (4-fluorophenyl)-2-thienyl-, (4-methoxy-{1,1'-biphenyl}-3-yl)hydrazone; and 9H-fluoren-9-one, 2,7-dichloro-, (4-methoxy-{1,1'-biphenyl}-3-yl)hydrazone.

16. The method of claim 11 wherein the coupling catalyst is a transition metal catalyst.

17. The method of claim 16 wherein the transition metal catalyst is selected from the group consisting of soluble and insoluble complexes of platinum, palladium, and nickel.

18. The method of claim 11 wherein the ligand is a phosphine ligand.

19. The method of claim 18 wherein the phosphine ligand is selected from the group consisting of tri-tert-butylphosphine, 2-(di-tert-butylphophino)biphenyl, 2-(dicyclohexylphosphino)biphenyl, bidentate phosphine ligands, and bis(phosphine) ligands.

20. The method of claim 11 wherein the first base is selected from the group consisting of alkoxides, alkali metal carbonates, alkali metal phosphates, alkaline earth carbonates, and alkaline earth phosphates.

21. The method of claim 11 wherein the solvent is selected from the group consisting of ethers, halogenated solvents, aliphatic hydrocarbon solvents, aromatic hydrocarbon solvents, esters, and ketones, polar aprotic solvents, or combinations thereof.

22. The method of claim 21 wherein the solvent is selected from the group consisting of toluene, dimethoxyethane, and tetrahydrofuran.

23. The method of claim 11 wherein the second base is pyridine.

* * * * *